(12) United States Patent
Kucharczyk et al.

(10) Patent No.: US 6,599,274 B1
(45) Date of Patent: Jul. 29, 2003

(54) CELL DELIVERY CATHETER AND METHOD

(76) Inventors: John Kucharczyk, 1050 Lane Creek Ct., Bishop, GA (US) 30621; George T. Gillies, Department of Mechanical and Aerospace Engineering, University of Virginia, P.O. Box 400746, Charlottesville, VA (US) 22904-4746; William C. Broaddus, Department of Neurosurgery, Virginia Commonwealth University, P.O. Box 980631, Richmond, VA (US) 23298-0631; Helen L. Fillmore, Department of Neurosurgery, Virginia Commonwealth University, P.O. Box 980631, Richmond, VA (US) 23298-0631

( * ) Notice: Subject to any disclaimer, the term of this patent is extended or adjusted under 35 U.S.C. 154(b) by 0 days.

(21) Appl. No.: 09/574,857

(22) Filed: May 19, 2000

Related U.S. Application Data

(60) Provisional application No. 60/177,263, filed on Jan. 20, 2000.

(51) Int. Cl.[7] ............... A61M 25/00; A61M 5/00
(52) U.S. Cl. ............... 604/264; 604/57; 604/60; 604/93.01; 604/164.01; 604/522; 606/15
(58) Field of Search ............... 604/27, 28, 48, 604/500, 522, 57, 59–62, 64, 68, 70, 72, 158–160, 93.01, 95.01, 95.02, 164.01, 164.02, 164.13, 170.01, 170.02, 264, 266; 606/13–15

(56) References Cited

U.S. PATENT DOCUMENTS

| | | | | |
|---|---|---|---|---|
| 5,423,744 A | * | 6/1995 | Gencheff et al. | 604/522 |
| 5,487,739 A | * | 1/1996 | Aebischer et al. | 604/93.01 |
| 5,906,599 A | * | 5/1999 | Kaldany | 604/264 |
| 6,045,532 A | * | 4/2000 | Eggers et al. | 604/114 |
| 6,061,587 A | * | 5/2000 | Kucharczyk et al. | 604/93.01 |
| 6,224,566 B1 | * | 5/2001 | Loeb | 606/15 |
| 6,299,583 B1 | * | 10/2001 | Eggers et al. | 600/526 |

* cited by examiner

*Primary Examiner*—Michael Powell Buiz
*Assistant Examiner*—Tuan Nguyen
(74) *Attorney, Agent, or Firm*—Beck & Tysver, P.L.L.C.

(57) ABSTRACT

A cell delivery catheter having one of more apearutres is used to positon and deliver cells to an implant site in a patient.

3 Claims, 3 Drawing Sheets

CELL DELIVERY CATHETER AND METHOD

This application claims the benefit of provisional application No. 60/177,263, filed Jan. 20, 2000.

FIELD OF THE INVENTION

This invention relates to both a catheter device and a method of using the catheter for inserting living cells into the body for the treatment of neurological disease.

BACKGROUND OF THE INVENTION

Deficits in neurotransmitters and other active biologic factors have been implicated in the etiology of various neurologic diseases. Parkinson's disease, for example, is characterized by a deficiency of the neurotransmitter dopamine within the striatum of the brain, secondary to damage or destruction of the dopamine secreting cells of the substantial nigra in the mesencephalon. To date, however, direct intraparenchymal delivery of purified or synthetic dopamine, or its precursors, analogs or inhibitors has not demonstrated clear therapeutic benefit. However these efforts have revealed various problems associated with drug delivery, stability, dosage and cytotoxicity of these agents.

In other disease states, biologically active macromolecules are believed to provide benefits by ameliorating the disease process or stimulating responses that result in therapeutic improvement. For example, models of Alzheimer's disease have been shown to benefit from the introduction of protein growth factors in vivo. Models of primary brain tumors have demonstrated therapeutic responses in response to the introduction of cytokines designed to stimulate the immune response against the tumor cells. However, it is difficult to provide reliable continuous delivery of these agents in actual clinical settings.

Implantable miniature osmotic pumps, such as disclosed, for example, by U.S. Pat. No. 4,475,916 to Himmelstein, et al. have been used to provide a continuous supply of drugs or other active biologic factors to the brain and other tissues at a controlled rate. Reservoir limitations as well as drug solubility and stability have, however, restricted the usefulness of this technology. Controlled sustained release of dopamine has been attempted from within bioabsorbable microcapsules, such as disclosed by U.S. Pat. No. 4,391,909 to Lim, U.S. Pat. Nos. 4,673,566, 4,689,293 and 4,806,355 to Goosen, et al., U.S. Pat. No. 4,803,168 to Jarvis and U.S. Pat. No. 4,883,666 to Sabel, et al. However, this method, appears to rely on surface erosion of the bioabsorbable polymer, which is in turn influenced by various hydrolytic events, thereby increasing the likelihood of drug degradation, and rendering predictable release rates difficult. A further problem appears to be attributable to limited diffusional surface area per unit volume of larger size microspheres, such that only a limited volume of cells can be loaded into a single microcapsule.

Exemplary of an implantable microporous devices for drug delivery are also known from U.S. Pat. No. No. 3,993,072 to Zaffaroni, U.S. Pat. No. 4,298,002 to Ronel, et al., and U.S. Pat. No. 4,309,996 to Theeuwes. U.S. Pat. No. 5,104,403 to Brotsu, et al., discloses a vascular prosthesis with a low porosity outer material and a inner synthetic tubular mesh. The semi-permeable microcapsules contain hormone producing cells that are placed between the outer material and the inner mesh. Blood flows through the vascular prosthesis allows for metabolism of the cells and circulation of the hormones. U.S. Pat. No. 5,171,217 to March, et al discloses a method for delivering drugs to smooth muscle cells lining blood vessels utilizing balloon catheter procedures and direct pressure delivery. However, the Brotsu et al. device does not involve the MRI-guided intraparenchymal delivery and monitoring of cell therapy.

Macroencapsulation, which generally involves loading cells into hollow fibers and then sealing the ends of the fibers, has also been used to deliver therapeutic drugs into the central nervous system. Exemplary of the macroencapsulation approach to drug delivery is U.S. Pat. No. 4,892,538 to Aebischer, et al., which discloses methods for delivery of a neurotransmitter to a target tissue from an implanted, neurotransmitter-secreting cell culture within a semi-permeable membrane, wherein the surgically implanted cell culture device may be retrieved from the brain, replaced or recharged with new cell cultures, and re-implanted. U.S. Pat. No. 5,106,627 to Aebischer et al. additionally discloses a method for the combined delivery of neurotransmitters and growth factors from implanted cells encapsulated within a semi-permeable membrane. However, while these methods may offer the advantage of easy retrievability, the encapsulation of cells within macrocapsules implanted in the brain is often complicated by unreliable closure of the reservoir resulting in inconsistent tresults.

Studies utilizing implantation of cells capable of producing and secreting neuroactive factors directly into brain tissue have demonstrated that Parkinson's disease symptoms can be improved by transplanting fetal dopamine cells into the putamen of the brain of patients with Parkinson's disease. U.S. Pat. No. 5,487,739 to Aebischer, et al. discloses a cell therapy delivery method utilizing a cannula, obdurator, and implantable cells, wherein the biologically active factors diffuse into brain tissue through an implanted semi-permeable membrane. U.S. Pat. No. 5,006,122 to Wyatt, et al. discloses an apparatus for transplanting tissue into a brain, comprising a stereotactic device for inserting a guide cannula to a target location within the brain into which a second cannula containing the tissue transplant is inserted and the tissue is deposited.

However, a major problem for this emerging therapy is the limited and variable supply of human fetal tissue and the societal issues associated with its use. Fetal pig neural cells have also been shown to survive in an immuno-suppressed parkinsonian patient. Improvements in the quality of transplantation also appear to be emerging. Recent studies have demonstrated that somatic cell cloning can efficiently produce transgenic animal tissue for treating parkinsonism. It is also possible to surgically remove neural progenitor cells from a patient, grow the cells in culture, insert therapeutic genes, and then replace the transfected cells back into the patient's brain.

Thus, there exists a need for an improved method to deliver cells that can produce biologically active factors to a target region of the brain. In addition, there is a need for a method to monitor non-invasively the ongoing viability of the cell implant, in particular to determine whether the cells are adequately perfused by the local microvasculature and continue to provide sustained and controlled delivery of the deficient biologically active factor.

SUMMARY OF THE INVENTION

The catheter of the present invention delivers cells, cell suspensions, or solid tissue grafts into the Central Nervous System (CNS) and in particular into a targeted region of the brain. Although the invention is disclosed in the context of the treatment of the brain it should be understood that spinal cord, and other target regions of a patient suffering from a debilitating neurologic condition or syndrome are amenable to the devices and techniques described herein.

The catheter device facilitates the use of imaging methods for the local and controlled delivery of a biologically active factor, which can augment or replace the function of dysfunctional constituents of the brain, spinal cord or other tissue without causing trauma.

The device and method of this invention facilitate and permit an imaging method for monitoring non-invasively whether the cell implant provides sustained and controlled delivery of the deficient biologically active factor.

Catheters according to the invention provide structures that shade or shutter certain apertures at the distal end of the catheter, thus allowing the clinician to more precisely regulate the delivery of diagnostic and/or therapeutic agents into the target tissues. The catheter architecture may also be used for controlling the amount of illumination that is delivered into the CNS through an optical fiber inserted through one of the catheter lumens. In this instance the light energy is used for assaying cells tagged with the green fluorescent protein or related materials.

In the method of the invention, conventional MRI navigation procedures are used to guide an MR-compatible access device and a catheter containing the cell implant to a target location in the brain or other tissue. Following the positioning of the catheter tip at the target location, delivery of the cell implant is monitored using high-resolution MR imaging in combination with optical or other imaging methods. Further in the method of the invention, high-resolution MRI methods may be used to non-invasively evaluate the viability of implanted cells.

BRIEF DESCRIPTION OF THE DRAWINGS

Illustrative embodiments of the invention are shown in the figures where like numerals represent like structures.

DETAILED DESCRIPTION

Figure 1:
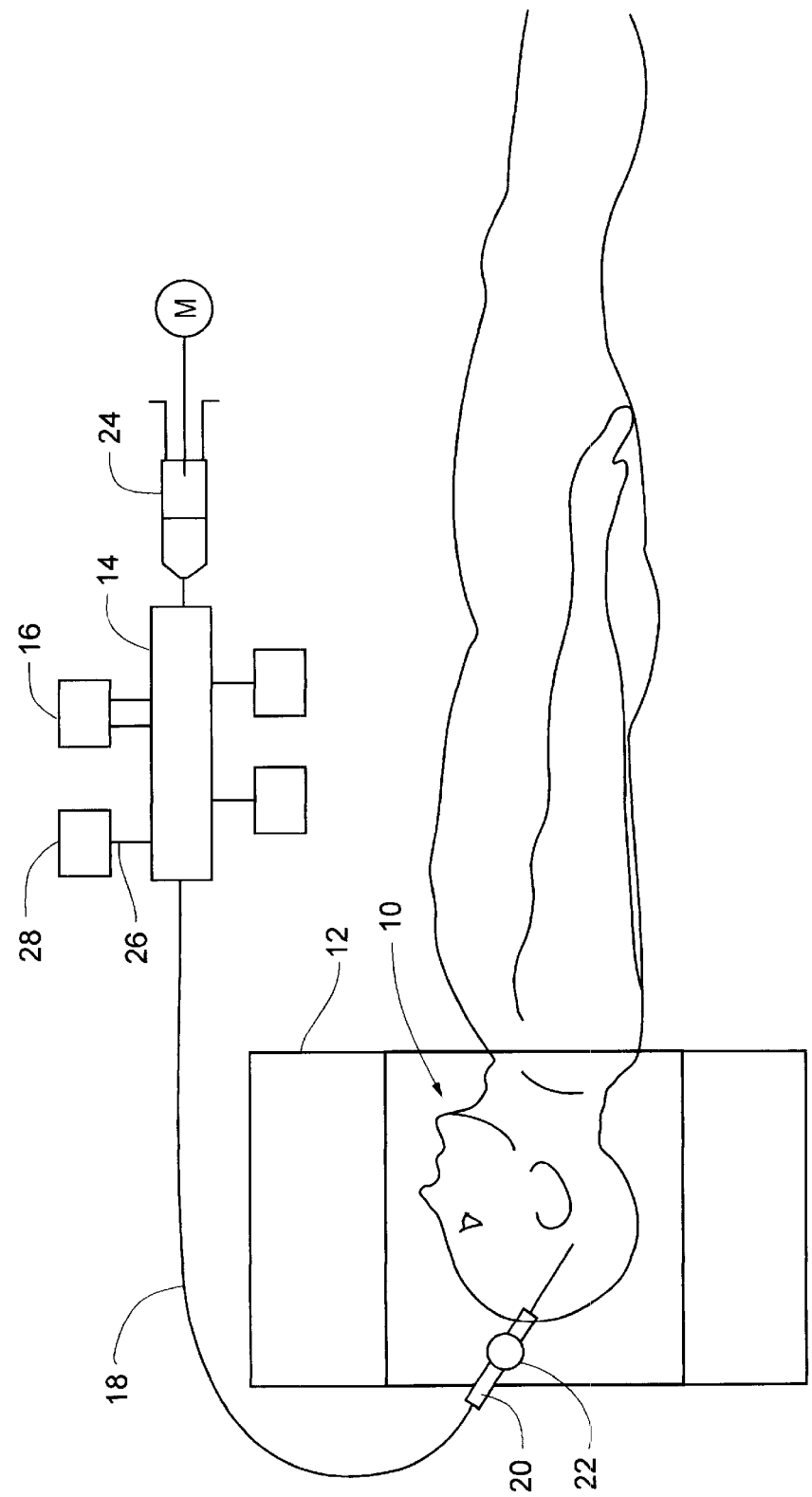
FIG. 1 shows a patient undergoing an MRI directed procedure to implant cells using the catheter.

FIG. 1 shows a patient 10 undergoing an intervention in an MRI magnet 12. The manifold 14 couples several therapeutic or diagnostic devices typified by device 16 to the cell delivery catheter 18. The cell delivery catheter 18 in turn is delivered through a guide sheath 20 that is positioned in a navigation guide 22. In operation the physician user inserts the catheter 18 into the brain under MRI guidance. The same or similar MRI visualization is used to follow the progress of the implant both acutely and chronically.

Figure 2:
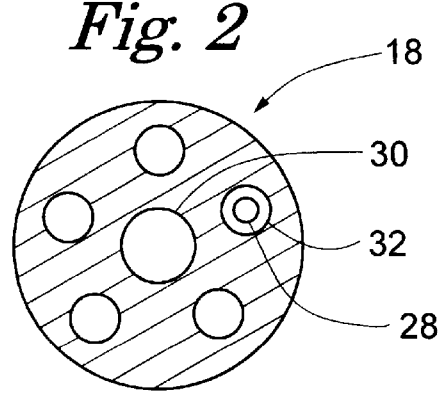
FIG. 2 shows a schematic diagram of the distal end of one embodiment of the multi-lumen catheter device used to deliver cells and intraparenchymal drugs.
Figure 3:
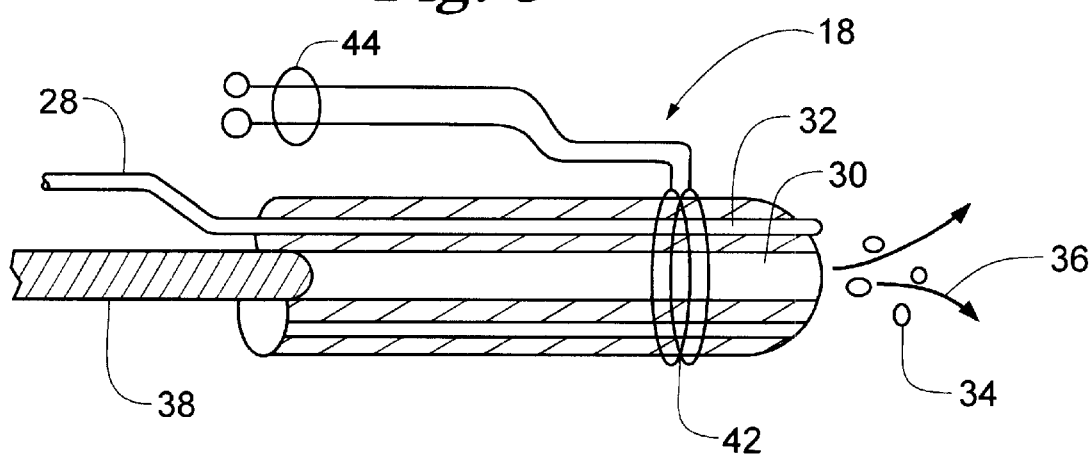
FIG. 3 shows a longitudinal cross sectional views of the device of FIG. 2.
Figure 4:
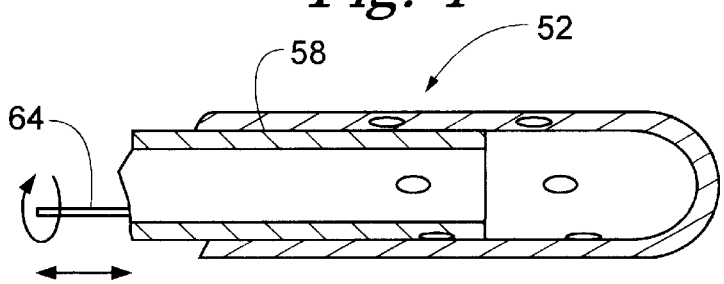
FIG. 4 shows a schematic longitudinal cross section of the distal tip of an alternate embodiment of a cell delivery catheter.
Figure 5:
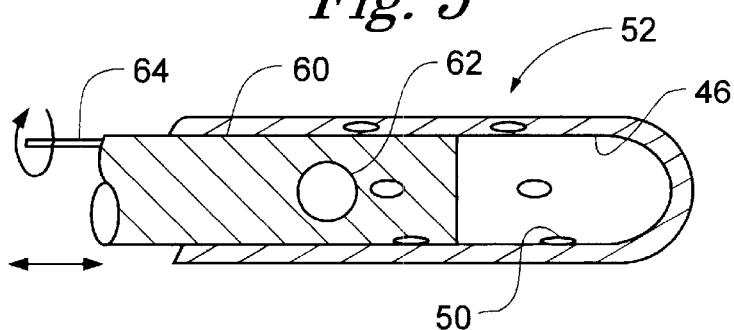
FIG. 5 shows a longitudinal cross section of the distal tip of an alternate embodiment of a cell delivery catheter.
Figure 6:
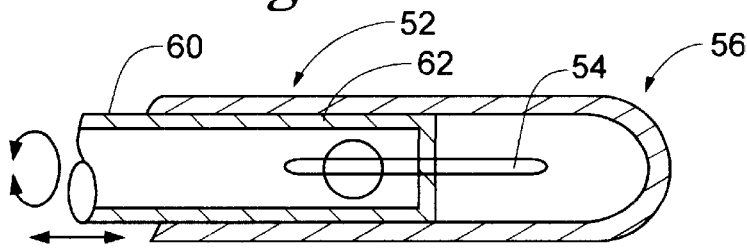
FIG. 6 shows a shows a longitudinal cross section of the distal tip of an alternate embodiment of a cell delivery catheter.

FIG. 2 depicts an embodiment of the catheter depicted in FIG. 1 and FIG. 3 in cross section. This version of the catheter 18 has a central barrel 30 that is surrounded by additional peripheral lumens typified by the peripheral lumen 32. These peripheral lumens may be used to deliver other devices and perform various diagnostic functions. Each lumen may communicate with a separate port of the manifold 14. For example lumen 32 may communicate with port 26 (FIG. 1). This lumen may contain a pressure transducer 28. Other lumens may be devoted to an optical cell counter device shown generically as device 16 in FIG. 1. Such a device may operate with two fibers located in two separate lumens and/or ports to measure the number of cells delivered by the catheter.

In the configuration of FIG. 2 and FIG. 3 it is preferred to use the central barrel 30 of the cell delivery catheter 18 for cell delivery, whereas the peripheral lumens typified by lumen 32 are used for device or drug delivery. Typically the device may be used for intraparenchymal delivery of drugs or other active biologic factors or therapeutic agents. As used herein, the term "biologically active factors" means neurotransmitters, neuroactive analgesic factors, as well as precursors, agonists, active analogs, and active fragments. We specifically include within this definition proteins, nucleic acids and other macromolecules having biologic activity, as well as agents that might be infused for their physical or chemical properties. Examples of biologically active macromolecules could include growth factors, cytokines, antibodies, hormones, oligonucleotides, modified long DNA constructs (synthetic vectors), glycoproteins and glycolipids. Examples of agents which might be infused for their physical properties could include radiographic contrast agents or reagents to enhance the in vivo detection of implanted cells or the products they have been engineered to produce. Also expressly included within the definition are cells that secrete neuroactive factors and hormones, including growth factors well known in this art.

According to the present invention, drug delivery is performed by infusion via convection efflux from a single lumen such as 32, or via a multiple peripheral ports (see FIG. 4, FIG. 5, FIG. 6 or FIG. 7) in order to facilitate broad spatial distribution of the drug within the region of the cell implant.

One of the significant problems with delivering cells directly into the brain or other tissues is to assure that the cells are accurately delivered to a target location and thereafter remain viable. According to the present invention, MRI navigation procedures are used to guide an MR-compatible intracranial access device, which is used in combination with a catheter containing the cell implant to reach a target location in the brain or other tissue.

Following MRI-guided positioning of the catheter tip at the target location, delivery of the cell implant is monitored using high-resolution MRI.

In the method of the invention, high-resolution MRI methods, most preferably diffusion tensor imaging are used to evaluate the viability of the cell implant based on the contiguity of cell-to-cell membranes within the cell implant following the delivery of the cell implant into the target location in the brain. MR imaging, most preferably diffusion coefficient imaging is used to evaluate fluid-electrolyte homeostasis in the extra- and intra-cellular fluids contiguous to the cell implant. Further in the method of the invention, perfusion MRI, is used to evaluate the functional capillary density of the cell implant longitudinally over days, weeks, and months in order to confirm that the cell implant has adequate perfusion to sustain its viability, especially with respect to its secretory functions. Also in the method of the invention, evaluation of the metabolic effects on the cell implant of neurotrophic, angiogenic, and other biologically active factors is determined using MR spectroscopy and MR perfusion imaging.

FIG. 3 shows a typical delivery of cells 34 in a carrier fluid 36 from the central barrel 30 of the catheter 18. In this situation the surrounding peripheral lumens of the catheter typified by lumen 32 house any one of a combination of physiologic probes, including intracranial pressure probes, optical fibers and/or optical fiber bundles configured for conveying illumination and/or optical signals to and from the target tissues, iontophoresis probes, thermometry probes, blood-flow-sensing probes, chemical probes, vacuum lines, fluid delivery tubes and conduits, guidewires, fixed and adjustable-tipped steering probes and wires, electric and magnetic field-sensing probes, electrodes and applicators, gene analysis chips and "lab-on-a-chip" structures, biopsy devices, tissue and cell implantation devices, cryogenic probes, cauterizing probes and tips, stents, coils, angioplasty balloons and devices, radioactive sources, magnetic and electric field sources, integrated circuits and other electronic devices. In FIG. 2 and in FIG. 3 the lumen 32 is "filled" with a pressure transducer 28 as an exemplary and non limiting example. The cells, in a fluid-based 36 suspension, may be manually pumped through the central barrel 30 with a manually operated syringe 24. Alternatively a programmed motor driven syringe can be used to control the infusion of the cell slurry into the brain. Alternatively, either a slurry containing the cells or an ensemble of small biodegradable packets containing the cells might be pushed through the central barrel 30 by an obdurator 38 or some other plunger mechanism. Alternatively, the cells (or packets of them) might be pushed down into the distal end of the catheter, and then held in place within the catheter by the obdurator or plunger, while the catheter 18 is withdrawn over the obdurator, thus leaving the cells in place following the subsequent removal of the obdurator and outer catheter 18. There are some cases where packaging and delivery of the cells in this manner would be desirable, particularly to avoid immune-response rejection of the cells, or to prevent damage to the cells during the course of the delivery process. Certain fibroblast cells that secrete nerve growth factors are packaged in polycarbonate encapsulation for these reasons. In other cases, containment of the cells might be counter-productive (even if they are encapsulated in substances that biodegrade in 24 hours or less), since encasement of the cells might prevent them from making biological connections with other cells already in the surrounding host tissues.

In still another embodiment, the slurry containing the cells 34 might be pumped through a re-circulating loop within the central barrel 30 (and possibly also through one of the auxiliary lumens) and passed through the gap between a coarse membrane and a re-entrant cavity at the tip of the catheter, thus permitting transport of the cells into the parenchymal millieu via the equivalent of cellular osmosis.

No matter how the cells are actually delivered, nutrients for them, growth factors or any other type of supplementary material might be infused into the brain either before, during or after the cell deposition process, through the same catheter 18.

FIG. 3 also shows several companion structures which may be used optionally to enhance the utility of the device. The RF coil 42 may be coupled to the MRI system to "image" the tip of the catheter. Although the RF coil is illustrated apart from the catheter 18 it would be integrated into the structure so that the connection 44 is within the body of the catheter and exteriorized at the proximal end of the device.

Although the central bore 30 design is effective it may be preferable to occlude the open distal lumen 30 with the obdurator 38 during insertion or navigation. The blunt distal tip of the catheter 18 along with the occluded central bore minimizes injury of the tissue during transport of the device to the therapy site.

In an alternate embodiment of the invention seen in FIG. 4, FIG. 5, FIG. 6, FIG. 7 and FIG. 8 a single lumen 46 of the device 18 or a single lumen catheter 52 itself would have an array of portholes typified by porthole 50 positioned axially along its distal end. The pattern of portholes or apertures may take the form of a spiral, or separate rings of apertures. The shape of the aperture is conveniently circular but alternate shapes are within the scope of the invention as well. For example a slit 54 (FIG. 6) may be used with a shade. It is preferred to have the distal tip 56 of the device 52 blunt and closed in these single lumen constructions.

Figure 7:
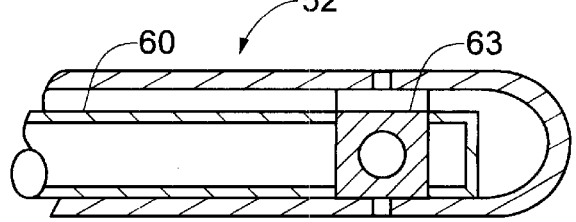
FIG. 7 shows a longitudinal cross section of the distal tip of an alternate embodiment of a cell delivery catheter; and, FIG. 8 shows a longitudinal cross section of the distal tip of an alternate embodiment of a cell delivery catheter.

The diagnostic or therapeutic agent of interest, the cell slurry, or any nutrient agents for the cells could be delivered into the CNS by pumping them through these portholes. To optimize the delivery process, a shutter 58 may be inserted through the catheter 52 to selectively occlude some or all of these portholes in a manner deemed best by the clinician regulating the therapy. The shutter 58 of FIG. 6 has an open end and it may select some or all of the distal portholes by retraction along the axis of the catheter 52. The closed end shutter 60 has an aperture 62 which may be rotated and aligned axially to select one or a small number of portholes. These shutter devices 60 or 58 may be manipulated by a pliable, thin-walled cylindrical tube or guidewire stylet 64 connected to the shutter for insertion into and withdrawal from the lumen of the catheter. The shutter is preferably concentric with the lumen 46, and has a good enough fit so that the shutter can shade or occlude some or all of the catheter's portholes, thus allowing the clinician to let the agent infuse into the CNS only in specific locations. Alternatively, a shuttering insert could be placed inside the catheter's lumen. Another form of shutter is shown in FIG. 7 where a stent like section 63 of the shutter allows selection of one set of apertures along the length of the catheter distal section. This type of shutter also allows the delivery of an agent from the catheter at just one particular set of portholes. Variations of these themes could include multiple aperture shutters, that permit any/all of the portholes to be covered or uncovered, even fractionally. The therapy control system could even be arranged such that the guidewire used to position the shutter or shade could be automated and motor driven in order to implement any strategy for time-controlled variation of the infusion rates from any of the catheter's portholes. Particular concentration gradients of cells or other infusates could also be established within a given region of the target tissues by configuring the diameter and spacing of the port holes on the catheter and on the shutter or shade insert appropriately. Alternatively, one could establish a given concentration gradient by infusing the cells into the target region through the various lumens of the multi-lumen catheter, but at different rates and/or pressures for each lumen, thus regulating the resultant overall concentration in the target region.

A plurality of different slide or shutter mechanisms might be made available as part of the catheter kit for a given patient, to accommodate different infusate measurement conditions, infusate types, and MR imaging strategies. The ability to completely remove the shutter or shade means, particularly if it has embedded rf-coils, might be needed if this class of device is to be used in conjunction with conventional stereotactic procedures for positioning of the catheter tip within the CNS. The slide means might also have radio-opaque marker bands on it to facilitate localization of it via x-ray imaging or computed tomography.

A shutter or shade means might also be employed to let the clinician sample ICP at selected locations along the length of the porthole array portion of the implanted catheter.

A pair of opposed optical fibers at the tip of the catheter might be used to count the number of cells exiting the central barrel and thus being delivered into the brain. The two optical fibers might run down the length of the catheter, each occupying a different auxiliary lumen of the catheter. At or near the tip, the fibers would either be aimed at each other by bending them, or additional optical elements would be used to otherwise make the light beam exiting one of them visible to the other. With satisfactory optical design, the resolution of such a system would make it possible to count cells as they are forced or drawn out of the catheter.

Figure 8:
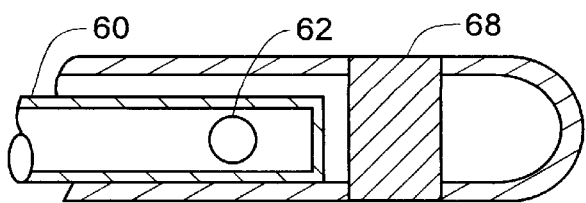

In another embodiment of the present invention seen in FIG. 8 a semipermeable membrane 68 along the distal end of the catheter preferably contains pores having a molecular weight exclusion of approximately 250 kD. The term "semipermeable," as used herein, means biocompatible membranes that permit the transport of molecules having a preselected low molecular weight, such as for example, 250 kD, while excluding the movement of molecules with a relatively higher molecular weight. The semipermeable membrane can be made of various polymeric compositions such as polyvinylchloride, polyacrylonitrile, polyvinylidene, fluoride, polystyrene, polyurethane, polyamide, cellulose acetate, cellulose nitrate, polymethylacrylate, polysulfone, polytetrafluoroethylene (Teflon®), acrylic polymer, and derivatives, copolymers and mixtures thereof. They might be fabricated or manufactured from films, thin sheets, extrusions or any other forms of such materials.

In the method of the invention, the cells may include secretory cells which have been isolated from natural sources, or have been genetically engineered to produce neuroactive factors, growth factors, cytokines, antibodies, extracellular matrix components or neurohormonal agonists (peptides or bioactive amines), precursors, active analogs, or active fragments. In a preferred aspect of the invention, the cell is an allograft or a xenograft. Preferred cell types may include those dopamine-secreting cells from the embryonic ventral mesencephalic brain, from neuroblastoid cell lines, or from the adrenal medulla. Any cells that have been genetically engineered to express a neurotransmitter or its agonist, precursor, derivative, analog, or fragment which has similar neurotransmitter activity, or bioactive macromolecular factors (see above), can also be used to practice this invention. For example, genetically engineered fibroblasts or other cell types may be used.

In the treatment of Parkinson's disease, it is possible to surgically remove neural progenitor or stem cells from a patient, grow the cells in culture, insert therapeutic genes, and then replace the transfected cells back into the patient's brain. However, the ability to monitor correct cell placement non-invasively with MR imaging is not currently available. In one particularly preferred embodiment of the present invention, MR imaging is used to deliver cells which are stably transfected with a detectable marker such as the Green Fluorescent Protein (GFP) marker used to establish stable transfected cell lines, and for monitoring cell delivery under MR imaging. In particular, this vector can be used to stable transfect neural progenitor stem cells and thence for the subsequent monitoring of their intraparenchymal locations. The GFP expression can continue in dividing cells for well over 30 days without use of antibiotic resistance selection drugs such as G418. For instance, in a rat model of this effect studied by certain of the present co-inventors, there was a net loss of only 10% of the GFP expression following a 30-day period in cell culture. When transfected progenitor stem cells differentiate into neurons, they are not expected to divide anymore. Therefore, in a preferred embodiment of the present invention, clones that will be used for CNS implantation are identified by using antibiotic resistance selection to confirm that they are capable of maintaining GFP expression after differentiation into neurons.

In another embodiment of the invention, final cellular differentiation is designed to occur in situ after implantation. Some transfected cell clones will demonstrate stable expression of GFP and other engineered transgenes after final differentiation, and others may be less stable during differentiation. In the latter case, infusion of a selection drug following implantation may be used to select for continued expression of GFP and transgenes coding for bioactive proteins after differentiation.

In general, the technique is not limited to this particular fluorescent protein construct. Alternative constructs fluorescing at wavelengths other than those in the green part of the visible optical spectrum can also be used.

In another particularly preferred embodiment of the present invention, optical imaging is used in combination with MRI for cell implant localization and monitoring. Optical fibers and/or optical fiber bundles configured for conveying illumination at the appropriate wavelength for the cells transfected with GFP are used to monitor cell delivery from the catheter into the target brain tissue region.

Thus, according to the present invention, cells transfected with GFP are imaged with optical methods, as well as with high-resolution MR methods using high-field (1.5 tesla or greater) magnets and high gradient values (b>1000) applied in three orthogonal directions. The combination of optical imaging and MR imaging is used to differentiate GFP transfected cells from other cells in the tissue volume adjacent to the cell implant based on their apparent diffusion coefficient differences.

Ultraviolet light used in the process of monitoring GFP transfected cells via optical fiber systems can result in photobleaching of the cells and cessation of their fluorescence. This could hinder use of the GFP technique for optically identifying the location of the cells of interest. A remedy to this potential problem is the use of vectors with inducible or repressible promoters that can modulate the expression of GFP and thus turn the fluorescence property on and off. Examples of such systems are the "Tet-On" and "Tet-Off" promoter/repressor systems, in which clinically used antibiotics, such as tetracycline or doxycycline, can be used to control the expression of the transfected genes. The availability of such systems means that photobleaching effects can be nullified by enabling expression of GFP only when needed for intraparenchymal optical imaging techniques.

Another significant aspect of intraparenchymal therapeutics requires the efficacious delivery of therapeutic agents as close to their receptors in the brain as possible, while minimizing increases in intracranial pressure attributable to the administered drug or the cell implant itself. In the method of the present invention, drug delivery into the parenchymal tissues can then be carried out via positive pressure infusion, or by diffusion-based delivery of pharmacological agents via the microdialysis process, using available lumens within the catheter to carry out either form of treatment.

Fluid-based drug agents and other liquids delivered into the brain through implanted catheters will disperse from the site of injection at variable rates depending on a number of factors, including the physicochemical characteristics of the drug, capillary uptake, metabolic degradation and excretion of the drug, size of the extracellular space, geometry of the brain cell microenvironment and input flow-rate and line pressure of the infusion system or other device that is pumping the drug into the brain. The degree to which each of these factors influences the distribution of a particular drug agent may be an important determinant of the effectiveness of drug treatment of diseases of the central nervous system.

Ideally, the injected material infiltrates the extracellular space, and the subsequent distribution of the drug within the tissues is governed mainly by its molecular weight, molecular radius, the structure and hydraulic conductivity of the tissue matrix into which the material has been injected, and the hydrodynamics of the infusion process. However, various flow scenarios may lead to tissue selling, an increase in ICP and, secondarily, altered interstitial transport of the drug solute or macromolecular species.

The transport of an infused solute in swelling tissues has been described mathematically by Basser using the expression $P_r=Q/4\pi r\ k$, where P is the pressure at the exit of the catheter, Q is the flow rate, r is the radial distance from the source, and k is the hydraulic conductivity of the tissues.

Increases in ICP induced by intraparenchymal injections of liquid drug agents or following cell implants can injure tissues directly (by pressure-induced cell membrane perturbations), or indirectly (by inhibiting the efficacious distribution of the drug due to tissue swelling and retarded interstitial solute transport). Thus, it is advantageous and potentially important to monitor any local and regional increases in ICP resulting from injections of liquid drug agents directly into the brain parenchyma.

Current methods of catheterization of the parenchymal tissues of the brain make it possible to measure intracranial pressure, deliver drugs in a rate-controlled manner, infuse various substances into the brain, and convey fluids out of the brain.

In the method of the present invention, a feedback mechanism is used to automate and optimize the monitoring of cell viability, wherein a number of physiological variables can be taken into account by the algorithm that governs the therapeutic response of the catheter system. In a preferred embodiment, physiological and metabolic data on the status of the patient (derived form other sensors on/in the body, such as, for example, probes or apparatuses which monitor tissue oxygen levels, blood flow, and other physiologic parameters) can be incorporated into the algorithm's treatment optimization process.

In a preferred embodiment of the method of the invention, the algorithm governing the patient's therapy preferably utilizes proportional-integral-derivative (PID) control functions, adaptive control functions, nonlinear control functions, multi-variable/state-space control functions, stochastic control functions and/or any other functional approach deemed appropriate for the implementation of the therapy. In all such cases, the controller could be designed to respond to changes in the patient's condition using artificial intelligence or other cybernetic techniques that would let the feedback mechanism "learn" the best way to respond to changes in the patient's physiological or anatomical status. Such techniques might employ, among other techniques, "fuzzy logic" algorithms that can function in the presence of incomplete or indeterminate data.

In the preceding detailed description of the preferred embodiments, references made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical, physical, computational, medical, architectural, and electrical changes may be made without departing from the spirit and scope of the present invention. The preceding detailed description is, therefore, not to be taken in a limiting sense, and the scope of the present invention is defined only by the appended claims and their equivalents.

What is claimed is:

1. A cell delivery catheter system for delivering and positioning cells in a patient's body operable by a user comprising:

a catheter body having a proximal end and a distal end, said catheter body defining a central axis; said catheter body fixed with respect to said patient body such that the catheter cannot move during use, said catheter body having at least one aperture located orthogonal to said central axis; said aperture being elongate along said axis to define a plurality of delivery locations;

a cell delivery barrel located within said catheter body having a distal aperture, said cell delivery barrel adapted to hold cells; said cell delivery barrel having at least one aperture orthogonal to said central axis, and movable with respect to said fixed catheter body to selectively align with said catheter body to control the delivery rate and delivery location of said cells at one of several locations along the central axis;

a source of fluid coupled to said cell delivery barrel for ejecting said cells from said cell delivery barrel under the control of a user.

2. The cell delivery catheter system of claim 1 wherein extension of the cell delivery barrel determines the location of cell delivery and the angular rotation of the cell delivery barrel determines the aperture size and therefore the delivery rate when said source of fluid is a manually operated syringe controlled by said user.

3. The cell delivery catheter system of claim 1 wherein extension of the cell delivery barrel determines the location of cell delivery and the angular rotation of the cell delivery barrel determines the aperture size and where said source of fluid is a motorized syringe controlled by said user.

* * * * *